(12) United States Patent
Plascencia, Jr. et al.

(10) Patent No.: US 9,358,061 B2
(45) Date of Patent: Jun. 7, 2016

(54) IRRIGATED CATHETER WITH FLUID EVACUATION

(71) Applicant: BIOSENSE WEBSTER (ISRAEL) LTD., Yokneam (IL)

(72) Inventors: Rogelio Plascencia, Jr., Rancho Cucamonga, CA (US); Dean Ponzi, Glendora, CA (US); Arnold Tuason, Claremont, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 170 days.

(21) Appl. No.: 13/679,907

(22) Filed: Nov. 16, 2012

(65) Prior Publication Data

US 2014/0142569 A1    May 22, 2014

(51) Int. Cl.
*A61B 18/14* (2006.01)
*A61B 18/08* (2006.01)
*A61B 18/00* (2006.01)
*A61B 19/00* (2006.01)

(52) U.S. Cl.
CPC ........... *A61B 18/082* (2013.01); *A61B 18/1492* (2013.01); *A61B 2018/00029* (2013.01); *A61B 2018/00035* (2013.01); *A61B 2018/00166* (2013.01); *A61B 2018/00577* (2013.01); *A61B 2018/00821* (2013.01); *A61B 2019/5251* (2013.01); *A61B 2218/001* (2013.01); *A61B 2218/002* (2013.01); *A61B 2218/007* (2013.01)

(58) Field of Classification Search
None
See application file for complete search history.

(56) References Cited

U.S. PATENT DOCUMENTS

| | | | |
|---|---|---|---|
| 4,674,499 A | 6/1987 | Pao | |
| 5,167,622 A | 12/1992 | Muto | |
| 5,429,596 A | 7/1995 | Arias et al. | |
| 5,630,837 A * | 5/1997 | Crowley | 601/2 |
| 5,944,713 A | 8/1999 | Schuman | |
| 5,964,757 A | 10/1999 | Ponzi | |
| 6,090,106 A | 7/2000 | Goble et al. | |
| 6,179,824 B1 | 1/2001 | Eggers et al. | |
| 6,569,114 B2 | 5/2003 | Ponzi et al. | |
| 6,855,143 B2 | 2/2005 | Davison et al. | |
| 7,220,233 B2 | 5/2007 | Nita et al. | |

(Continued)

FOREIGN PATENT DOCUMENTS

EP    1 795 139 A1    6/2007
EP    2156801 A1    2/2010

(Continued)

OTHER PUBLICATIONS

Extended European Search Report issued in EP 13193205.5, dated Feb. 17, 2014, 9 pgs.

(Continued)

*Primary Examiner* — Kennedy Schaetzle
(74) *Attorney, Agent, or Firm* — Lewis Roca Rothgerber Christie LLP

(57) ABSTRACT

A catheter for use with a suction source for removing excess fluid from a tissue treatment site has a catheter body, a distal section and a fluid evacuation path, where the distal section includes a multi-lumened member and at least one evacuation port, and the fluid evacuation path extends through a lumen in the multi-lumened member to provide suction communication between the suction source and the at least one evacuation port. The fluid evacuation path may also be configured for two-way flow, including distally and proximally along the catheter.

9 Claims, 8 Drawing Sheets

(56) References Cited

U.S. PATENT DOCUMENTS

| | | |
|---|---|---|
| 7,326,235 B2 | 2/2008 | Edwards |
| 7,387,625 B2 | 6/2008 | Hovda et al. |
| 7,399,300 B2 | 7/2008 | Bertolero et al. |
| 7,744,595 B2 | 6/2010 | Truckai et al. |
| 2002/0002372 A1* | 1/2002 | Jahns et al. ............ 606/41 |
| 2002/0095152 A1 | 7/2002 | Ciarrocca et al. |
| 2010/0049119 A1 | 2/2010 | Norman et al. |
| 2011/0313286 A1 | 12/2011 | Whayne et al. |

FOREIGN PATENT DOCUMENTS

| | | |
|---|---|---|
| EP | 2301617 A1 | 3/2011 |
| WO | WO95/05771 | 3/1995 |
| WO | WO 01/95819 A1 | 12/2001 |

OTHER PUBLICATIONS

Extended European Search Report dated Feb. 6, 2015 in EP Application No. 14198442.7, 7 pages.

* cited by examiner

IRRIGATED CATHETER WITH FLUID EVACUATION

FIELD OF INVENTION

The present invention relates to an electrophysiologic catheter that is particularly useful for ablation and sensing electrical activity of heart tissue.

BACKGROUND OF INVENTION

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure—mapping followed by ablation—electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into a chamber of the heart. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the ablation electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than tissue, impedance to the flow of electrical energy into the tissue also increases. If the impedance increases sufficiently, an impedance rise occurs and the catheter must be removed from the body and the tip electrode cleaned.

In a typical application of RF current, circulating blood provides some cooling of the ablation electrode. Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the catheter. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

Another consideration is the ability to control the exact position and orientation of the catheter tip. This is ability is critical and largely determines the usefulness of the catheter. It is generally known to incorporate into electrophysiology catheters an electromagnetic (EM) tri-axis location/position sensor for determining the location of a catheter's distal end. An EM sensor in the catheter, typically near the catheter's distal end within the distal tip, gives rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

Where the distal tip is irrigated, fluid loading in the patient becomes a significant factor as ablation procedures can last five or six hours. Conventional irrigated tip electrodes typically operate with a flow rate of about 17 ml/minute at below about 30 watts of RF ablation energy to about 30-50 ml/minute at about 30 watts or greater. Moreover, current catheters include irrigated ring electrodes further increasing the fluid load in the patient. The pericardial space can quickly begin to fill with the irrigation fluid, such as saline, thereby limiting the amount of time the ablation catheter can be in the body and the number of ablations that can be performed due to fluid overload.

Accordingly, it is desirable that a catheter be adapted for removal of excess fluids by suction through fluid evacuation ports near the ablating electrodes.

SUMMARY OF THE INVENTION

The present invention is directed to a catheter for use with a suction source for removing excess fluid from a tissue treatment site. In one embodiment, the catheter has an elongated catheter body, a distal section and a fluid evacuation path, where the distal section has a multi-lumened member and at least one evacuation port, and the fluid evacuation path extends through a lumen in the multi-lumened member to provide suction communication between the suction source and the at least one evacuation port. The one or more evacuation ports may be formed in the multi-lumened member, or it may be formed in a tip electrode of the distal section extending distally from the multi-lumened member.

In another embodiment, the fluid evacuation path is configured for two-way flow, including distally and proximally along the catheter. The catheter is configured for operation in two modes: irrigation and evacuation. Irrigation fluid can be transported to the tissue treatment site and excess irrigation fluid and/or bodily fluids can be suctioned from the tissue treatment site and deposited in a collection chamber. In a detailed embodiment, the catheter includes a valve having a switch adapted to allow fluid and suction communication between the fluid path and the suction source or fluid communication between the fluid path and the irrigation fluid source. In a more detailed embodiment, the valve provides first, second and third connections, the first connection adapted for communication with the suction source, the second connection adapted for communication with the irrigation fluid source, the third connection adapted for communication with the fluid path.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
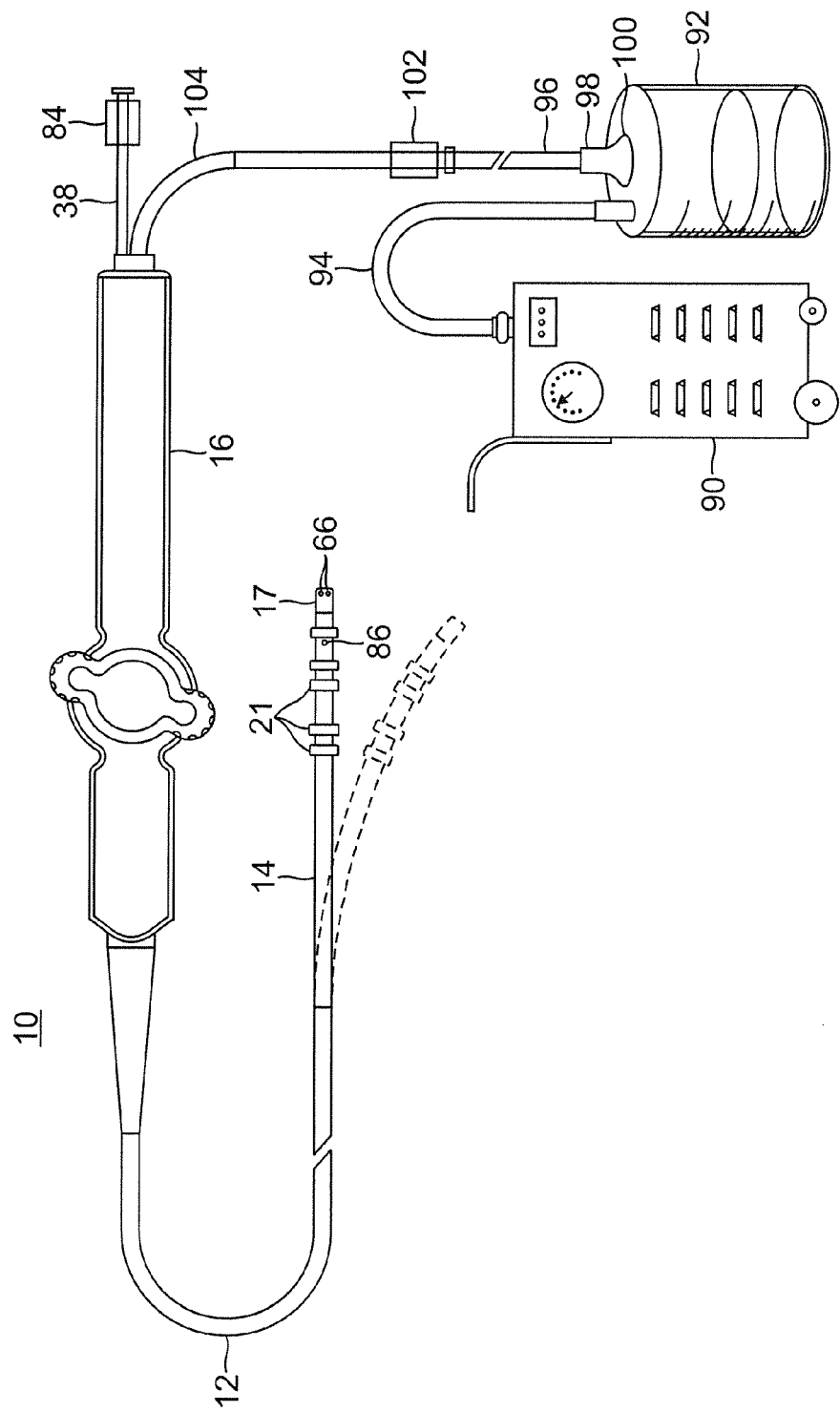
FIG. 1 is a perspective of a catheter according to an embodiment of the present invention, in use with a suction source and a fluid collection chamber.

In an embodiment of the invention, there is provided a steerable bi-directional catheter having an irrigated tip and fluid evacuation adaptations. As shown in FIGS. 1-3, catheter 10 comprises an elongated catheter body 12 having proximal and distal ends, a deflectable distal tip section 14 at the distal end of the catheter body 12, and a control handle 16 at the proximal end of the catheter body 12.

Figure 2A:
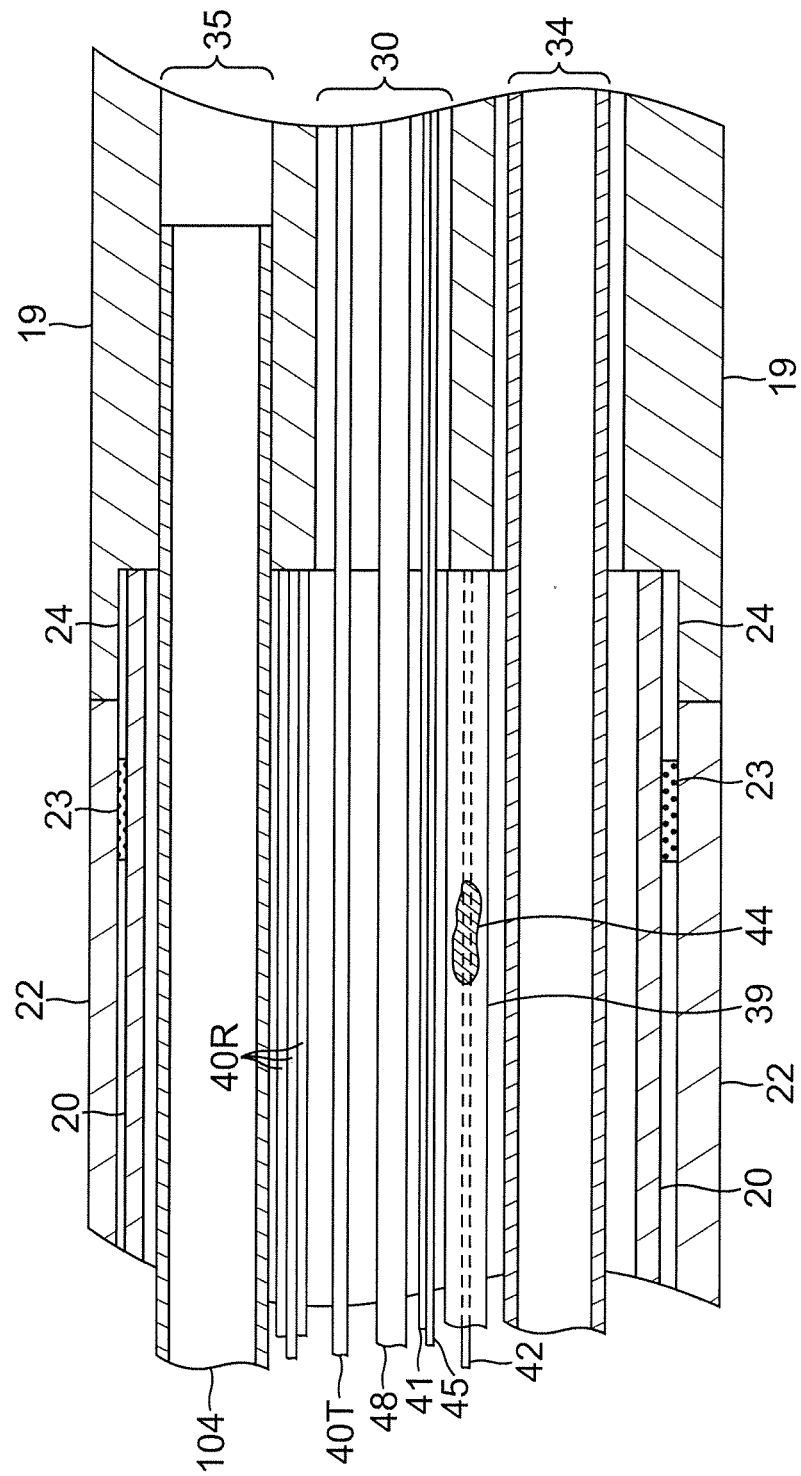
FIG. 2A is a side cross-sectional view of the catheter FIG. 1, showing a junction between a catheter body and a deflectable distal section, taken along a first diameter.
Figure 3:
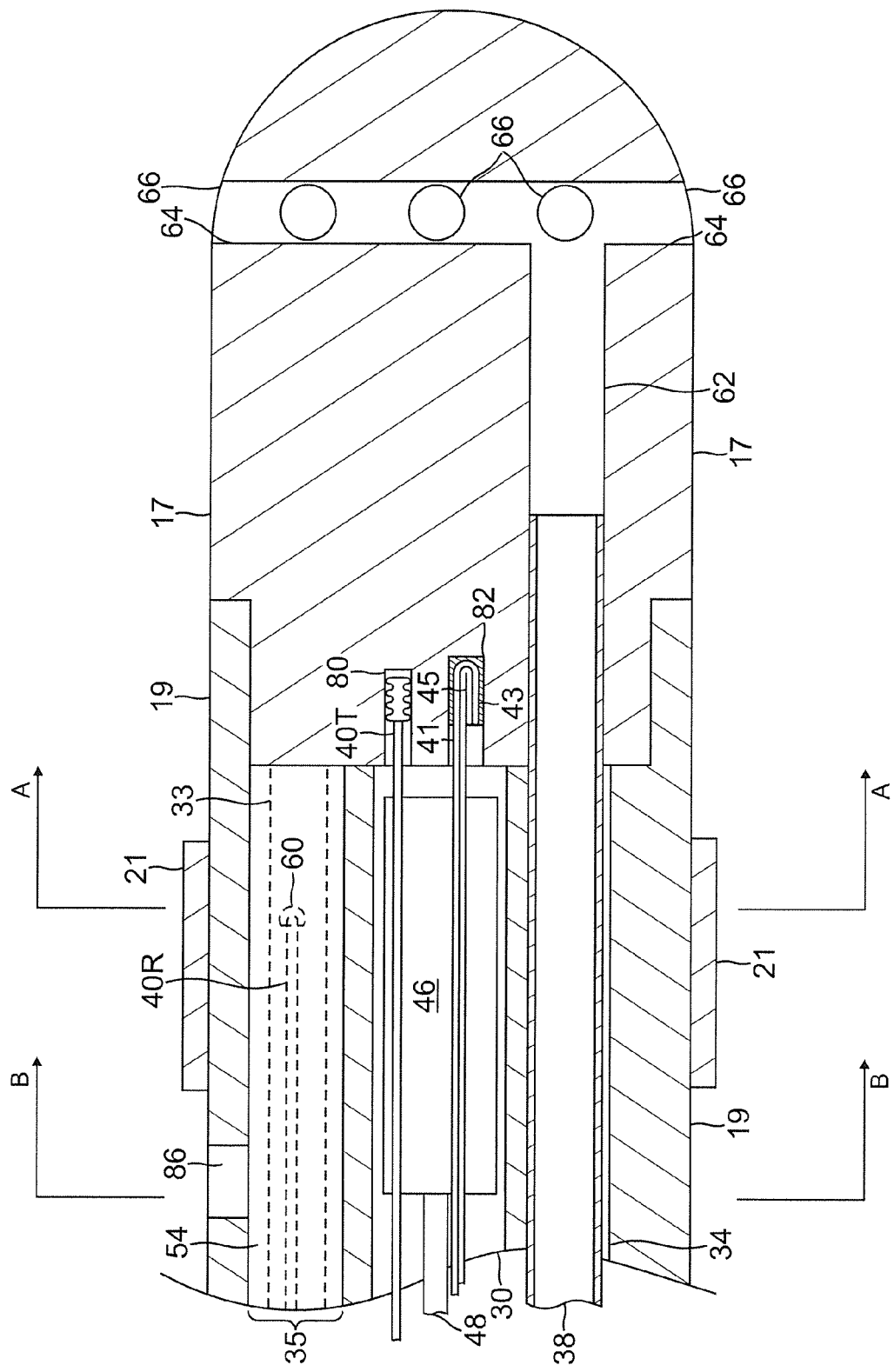
FIG. 3 is a side cross-sectional view of a distal section of the catheter of FIG. 1, taken along a diameter.

With reference to FIGS. 1 and 2A, the catheter body 12 comprises an elongated tubular construction having a single, axial or central lumen 18. The catheter body 12 is flexible, i.e., bendable but with substantially torsional stiffness. The catheter body 12 can be of any suitable construction and made of any suitable material. In the illustrated embodiment, the catheter body 12 has an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the single lumen 18 of the catheter body 12 are components, including lead wires, an irrigation tube, a first compression coil through which a first puller wire extends for uni-directional deflection, if not also a second compression coil through which a second puller wire extends for bidirectional deflection. Other components include a cable for a position sensor, thermocouple wires, and an evacuation tube. A single lumen catheter body is often preferred over a multi-lumen body because it has been found that the single lumen body permits better tip control when rotating the catheter. The single lumen permits the components to float freely within the catheter body. If such wires and tube were restricted within multiple lumens, they may build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components.

The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

An embodiment of the catheter has the outer wall 22 with an outer diameter of from about 0.090 inch to about 0.094 inch and an inner diameter of from about 0.061 inch to about 0.065 inch and the polyimide stiffening tube 20 having an outer diameter of from about 0.060 inch to about 0.064 inch and an inner diameter of from about 0.051 inch to about 0.056 inch.

At least one puller wire 42 for deflecting the tip section 14 extends through the catheter body 12. It is anchored at its proximal end to the control handle 16, and anchored at its distal end in the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated within the catheter body 12 in surrounding relation to a respective puller wire 42. The compression coil 44 extends from the proximal end of the catheter body 12 to about the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. Teflon® coating on the puller wire 42 allows it to slide freely within the compression coil 44. If desired, particularly if electrode lead wires are not enclosed by a protective sheath, the outer surface of the compression coil 44 can be covered by a flexible, non-conductive sheath 39, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint (not shown) and at its distal end to the tip section 14 by glue joint 51. Both glue joints preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

Figure 2B:
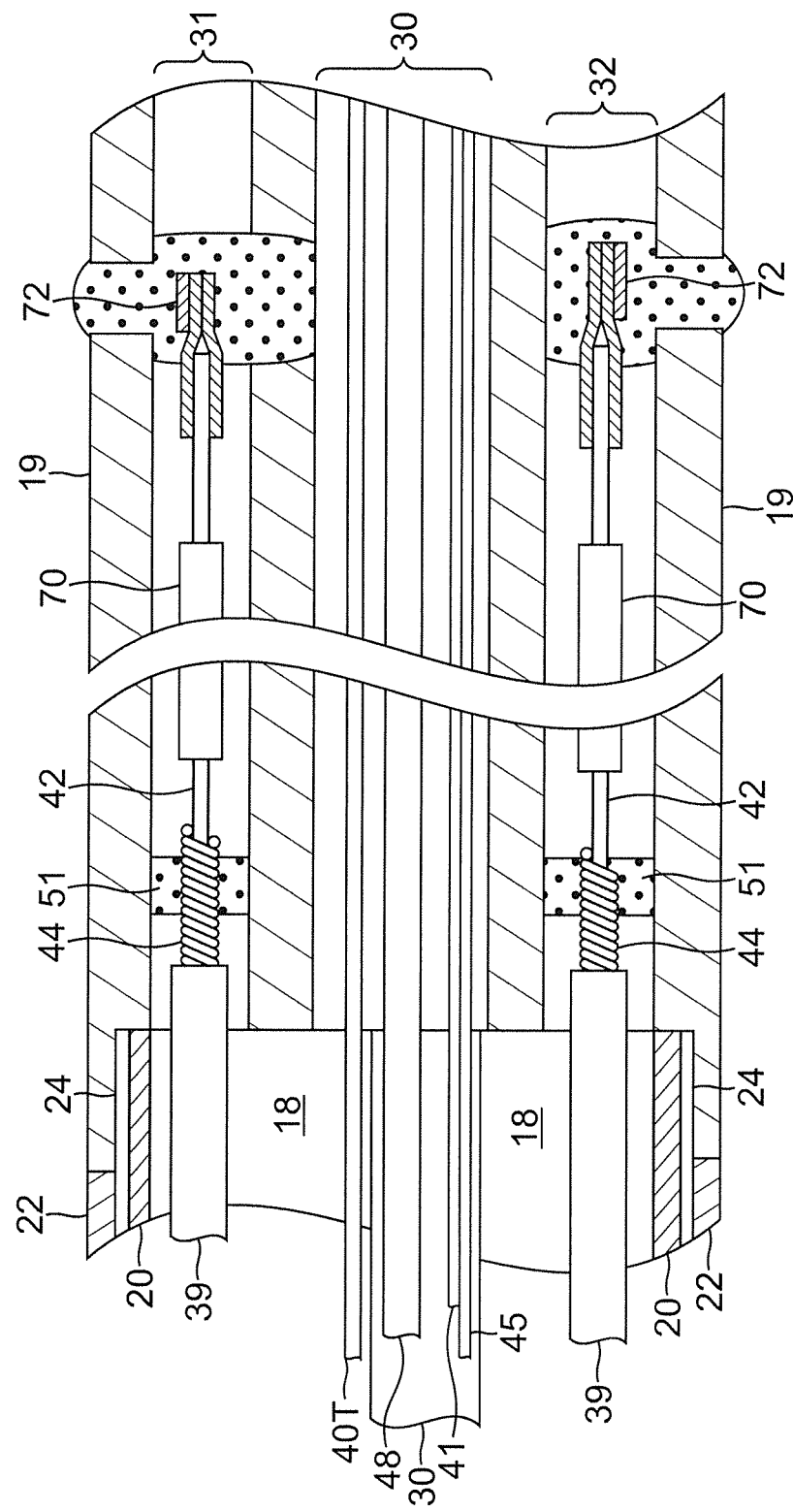
FIG. 2B is a side cross-sectional view of the catheter of FIG. 1, showing a junction between a catheter body and a deflectable distal section, taken a long a second diameter generally perpendicular to the first diameter.

With reference to FIG. 2B, the illustrated embodiment of the catheter 10 has a pair of puller wires 42 for bi-directional deflection, each having a respective compression coil 44 surrounding the puller wire from about a proximal end of the catheter body 12 to about a distal end of the catheter body 12.

The tip section 14 distal of the catheter body 12 carries a tip electrode 17 and a plurality of ring electrodes 21. The tip section 14 also carries an electromagnetic position sensor 46. A suitable means for attaching the catheter body 12 to the tip section 14 is illustrated in FIGS. 2A and 2B. The tip section 14 comprises a multi-lumened tubing 19, the proximal end of which comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint (not shown) is formed between the proximal ends of the stiffening tube 20 and outer wall 22 using a slower drying but more permanent glue, e.g., polyurethane.

If desired, a spacer can be located within the catheter body 12 between the distal end of the stiffening tube 20 and the proximal end of the tip section 14. The spacer provides a transition in flexibility at the junction of the catheter body 12 and tip section 14, which allows this junction to bend smoothly without folding or kinking. A catheter having such a spacer is described in U.S. patent application Ser. No. 08/924,616, entitled "Steerable Direct Myocardial Revascularization Catheter", the disclosure of which is incorporated herein by reference.

As shown in FIGS. 2A, 2B, 3A and 3B, the tubing 19 of the tip section 14 has multiple lumens, e.g., three or four or more lumens. The tubing 19 is made of a suitable non-toxic material that is preferably more flexible than the catheter body 12. One construction of the tubing 19 is braided polyurethane, i.e., polyurethane with an embedded mesh of braided stainless steel or the like, but the tubing 19 can comprise a plastic core, an inner plastic layer surrounding the core, a braided stainless steel mesh surrounding the inner layer, and an outer plastic layer surrounding the braided mesh. A suitable tubing is described in U.S. Pat. No. 6,569,114.

The outer diameter of the tip section 14, like that of the catheter body 12, is preferably no greater than about 8 french, more preferably 7 french. The size of the lumens is not critical. In one embodiment, the tip section 14 has an outer diameter of about 7 french (0.092 inch) and the tubing 19 contains six lumens, including a central, on-axis lumen 30 for lead wire 40T for the tip electrode 17, thermocouple wire pair 41 and 45, a cable 48 for the position sensor 46. A pair of diametrically opposed lumens 31, 32 are provided, each for a respective puller wire 42. Off-axis lumen 33 is provided for lead wires 40R for the ring electrodes 21. Off-axis lumen 34 is provided for an irrigation tubing 38. At least one off-axis lumen 35 is provided for at least one fluid evacuation path provided in the catheter 10. The lumens may have a diameter of ranging between about 0.018 inch and 0.029 inch.

Figure 3A:
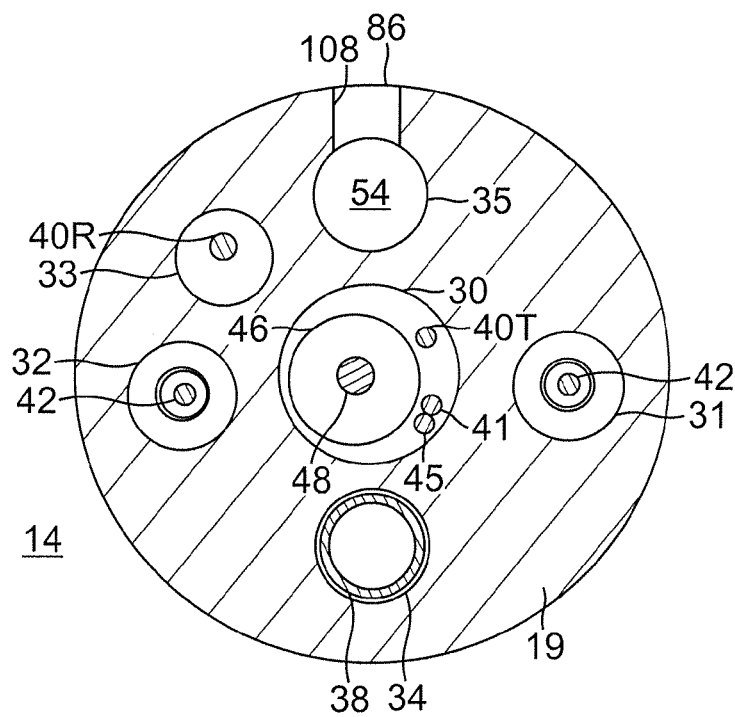
FIG. 3A is an end cross-sectional view of the distal section of FIG. 3, taken along line A-A.
Figure 3B:
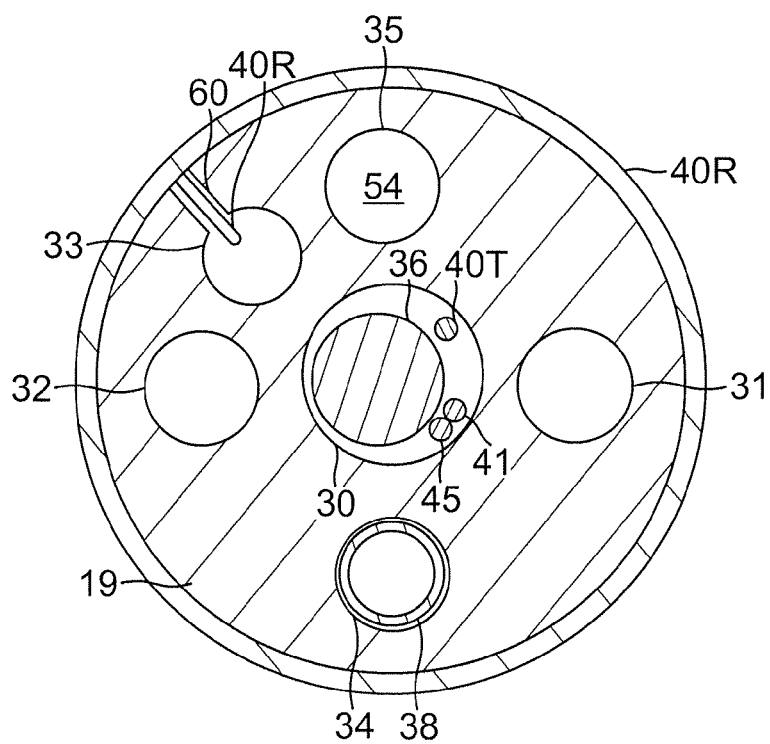
FIG. 3B is a side cross-sectional view of the distal section of FIG. 3, taken along line B-B.

As shown in the embodiment of FIGS. 3 and 3B, a proximal end of the tip electrode 17 is inserted into the distal end of the tubing 19 of the tip section 14. The proximal end of the tip electrode 36 is notched circumferentially to fit inside the distal end of the tubing 19. The notched proximal end may be bonded to the tubing 19 by polyurethane glue or the like. The wires, cable and irrigation tube that extend into the tip electrode 17 help keep the tip electrode attached to the tip section 14.

It is understood that the location and number of ring electrodes 21 may vary as desired. The ring electrodes may be configured for uni- and/or bi-polarity as desired. The tip and ring electrodes 17, 21 can be made of any suitable material, including platinum and/or iridium. The electrode lead wires 40T, 40R pass through the control handle 16, and terminate at their proximal end in an input jack (not shown) that may be plugged into an appropriate monitor (not shown). The portion of the lead wires 40T, 40R extending through the proximal end of the tip section 14, the central lumen 18 of the catheter body 12 and the control handle 16 are enclosed within a protective sheath (not shown), which can be made of any suitable material, preferably polyimide. The protective sheath is anchored at its distal end to the proximal end of the tip section 14 by gluing it in the lumens with polyurethane glue or the like.

Connection of lead wire 40T to the tip electrode 17 is accomplished, for example, by welding a distal end of the lead wire into a blind hole 80 (FIG. 3) formed in a proximal surface of the tip electrode. Connection of lead wire 40R to a ring electrode 21 is accomplished, for example, by first forming a small hole 60 (FIGS. 3 and 3B) through an outer wall of the tubing 19 by inserting a needle through the outer wall and heating the needle sufficiently to form a permanent hole. The lead wire 40R is then drawn through the hole by using a microhook or the like. The end of the lead wire 40R is stripped of any coating and soldered or welded to the underside of the ring electrode 21, which is then slid into position over the hole and fixed in place with polyurethane glue or the like.

The temperature sensing means provided in the tip section 14 may also be a thermistor such as Model No. AB6N2-GC14KA143E/37C sold by Thermometrics (N.J.). In the thermocouple however of the illustrated embodiment, the wire 41 is a number "40" copper wire, and the wire 45 is a number "40" constantan wire, which gives support and strength to the wire pair. The wires 41 and 45 of the wire pair are electrically isolated from each other except at their distal ends where they contact and are twisted together, covered with a short piece of plastic tubing 43, e.g., polyimide, and covered with epoxy. The plastic tubing 43 is then attached in a blind hole 82 formed in the proximal surface of the tip electrode 17, by polyurethane glue or the like. The wires 41 and 45 extend through the lumen 30 of the tubing 19 of the distal section 14, the central lumen 18 of the catheter body 12 and the control handle 16. Proximal of the control handle, the wires are connected to a connector (not shown) connectable to a temperature monitor (not shown).

A pair of puller wires 42 are provided for bi-directional deflection. Proximal ends of the puller wires are anchored in the control handle 16. The puller wires 42 extend through the control handle 16 and the central lumen 18 of the catheter body 12 (FIG. 2A). In the tubing 19 of the distal section 14, a first puller wire 42 extends through the lumen 31 and a second puller wire extends through the diametrically opposite lumen 32 (FIG. 3A). Distal ends of the puller wires are anchored near the distal end of the tubing 19 into a side wall of the tubing by T-bars 72 (FIG. 2B). Alternatively, a metal tubing of hypodermic stock can be crimped onto the distal end of each the puller wire 42 and soldered inside a blind hole formed in the proximal surface of the tip electrode 17.

The cable 48 for the electromagnetic sensor 46 extends through the lumen 30 of the tubing 19. Its distal end is connected to the sensor 46 (FIG. 3) which is fixedly attached inside the lumen 30 near the tip electrode 17 by polyurethane glue or the like.

The proximal end of the cable 48 extends out the proximal end of the control handle 16 within an umbilical cord (not shown) to a sensor control module (not shown) that houses a circuit board (not shown). The cable 48 comprises multiple wires encased within a plastic covered sheath. In the sensor control module, the wires of the electromagnetic sensor cable 48 are connected to the circuit board which amplifies the signal received from the electromagnetic sensor 46 and transmits it to a computer (not shown) in a form understandable by the computer.

The proximal end of the irrigation tube 38 extends through the control handle 16 and terminates in a luer hub 84 or the like at a location proximal to the control handle. In practice, fluid is injected into the irrigation tube 38 through the luer hub 84 (FIG. 1), and flows through the irrigation tube 38 extending through the central lumen 18 of the catheter body 12 and the lumen 34 of the tip section 14 in fluid communication with a fluid passage and transverse branches 64 in the tip electrode. Fluid thus travels into the tip electrode 17 via the fluid passage 62 and transverse branches 64 where it exits the tip electrode 17 via irrigation ports 66 provided at or near a distal end of the tip electrode 17.

The catheter of the present invention advantageously provides a fluid evacuation path in suction communication with at least one fluid evacuation port 86 in the tip section 14. In the illustrated embodiment of FIG. 1, the catheter is adapted for use with a suction source 90 and a fluid collection chamber 92 in suction communication with each other via a suitable suction conduit 94. The suction source 90, e.g., a suction pump or compressor, provides a vacuum or negative pressure in the fluid collection chamber 92. Extending from the fluid collection chamber 92 is a suction tube 96 whose proximal end is received in a connector 98 that is mounted on a connecting port 100 of the collection chamber 92. A distal end of the suction tube 96 is received in a connector 102 that provides connection with a proximal end of an evacuation tube 104 which extends through the catheter and provides suction communication between the suction source 90 and the evacuation ports 86.

The evacuation tube 104 extends through the control handle 16, through the central lumen 18 of the catheter body 12, and into the lumen 54 of the tip section 14. In one embodiment, the evacuation tube 104 terminates a short distance distal of the junction between the catheter body 12 and the tip section 14 although it is understood that the distal end may be located near or in the tip electrode 17. The evacuation tube 104 is sized and shaped to provide a fluid- and suction-tight seal with the lumen 54 which extends the length of the tubing 19 of the distal section 14. Near the distal end of the tubing 19, a radial evacuation through-hole 108 is formed in the side wall of the tubing 19 in communication with the evacuation port 86 to provide suction communication between the lumen 54 and the evacuation port 86. In the illustrated embodiment, three ports are formed along a circumference of the tubing 19 between a distal-most ring electrode 21 and an adjacent ring electrode 21b. The plurality of ports along a circumference can range between about one to six, and preferably between about three to four In operation, the catheter provides irrigation at the tissue ablation site. Irrigation fluid enters the catheter via the luer hub 84 and passes into the irrigation tubing 38 which extends through the control handle 16, the catheter body 12 and the distal section 14. The fluid enters the tip electrode 17 via the fluid passage 62, passes through the transverse branches 64 and exits to outside of the tip electrode via the irrigation ports 66. Irrigation fluid, such as saline, helps cool the tip electrode during ablation so as to minimize the formation of char on the tip electrode. To reduce fluid load on the patient, the evacuation path 54 advantageously provided in the catheter 10 allows the suction source 90 to draw fluids (including irrigation fluid and other bodily fluids) from the tissue ablation site and deposit the fluids in the collection chamber 92 via the suction tube 96. The suction communication and fluid communication between the evacuation tube 104 and the collection chamber 92 is established when the suction tube 96 and the evacuation tube 104 are connected via the connector 102.

During ablation by the tip electrode and/or the ring electrodes, irrigation fluid passes through the catheter 10 from the control handle 16 to the tip section 14 via irrigation tube 38 and exits the irrigation ports 66 in the tip electrode 17 (and/or the ring electrodes 21 where they are adapted for irrigation). With the suction source 90 activated, negative pressure is created in the collection chamber 92 via suction conduit 94 which creates suction in the suction tube 96 and the evacuation tube 104. Fluid encountered by the evacuation port(s) 86, including irrigation fluid delivered by the catheter to the ablation site, is drawn through the evacuation port(s) 86 and the evacuation tube 104 for deposit and collection in the collection chamber 92. Removal of excess fluid, especially irrigation fluid introduced by the catheter, decreases the risk of fluid overload thereby increasing the amount of time the catheter can be in the body and the number of ablations that can be performed on the patient.

Figure 4:
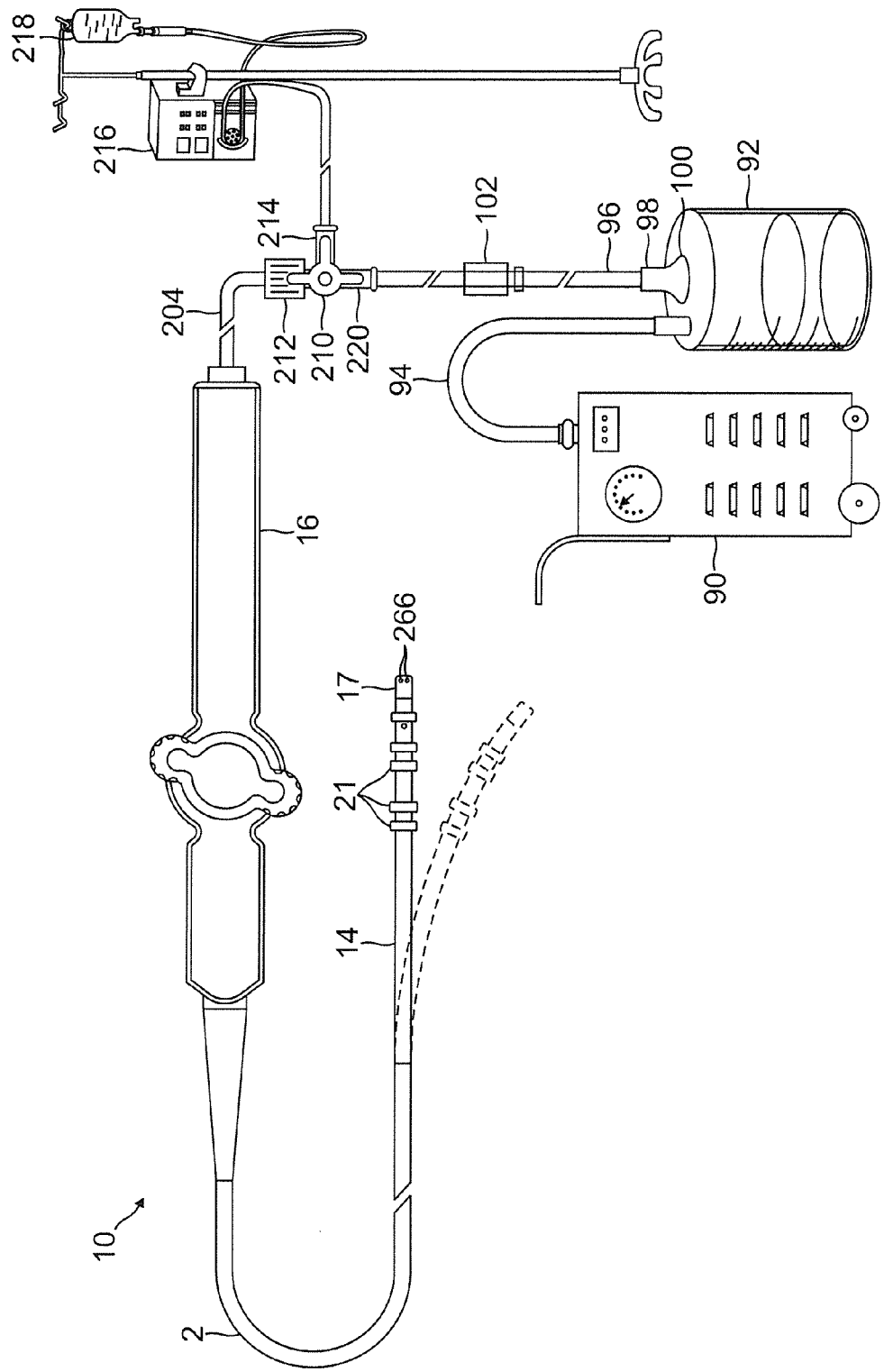
FIG. 4 is a perspective view of an alternate embodiment of a catheter of the present invention, for use with a suction source, a collection chamber and an irrigation fluid source.
Figure 5:
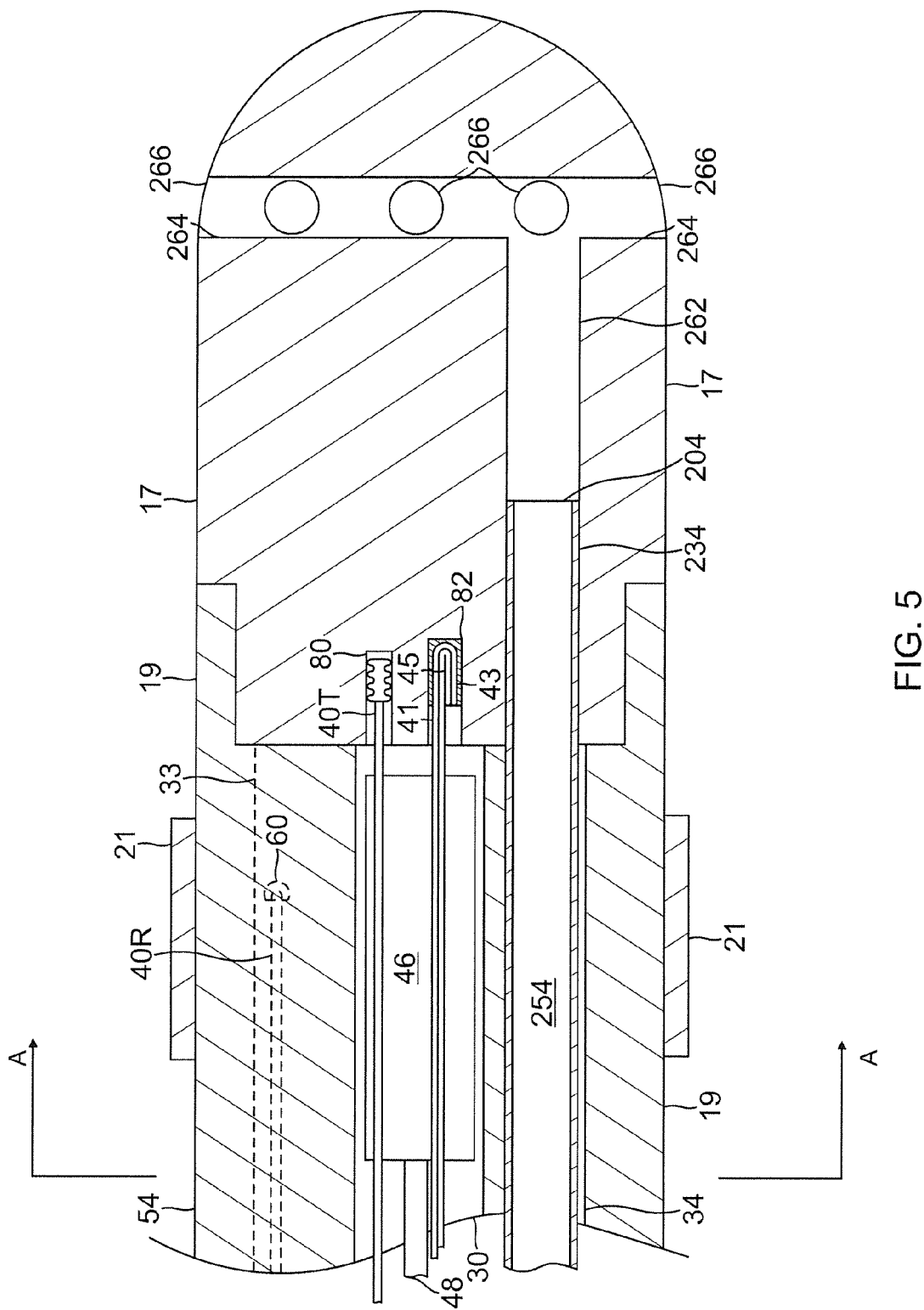
FIG. 5 is a side cross-sectional view of a distal section of the catheter of FIG. 4.
Figure 5A:
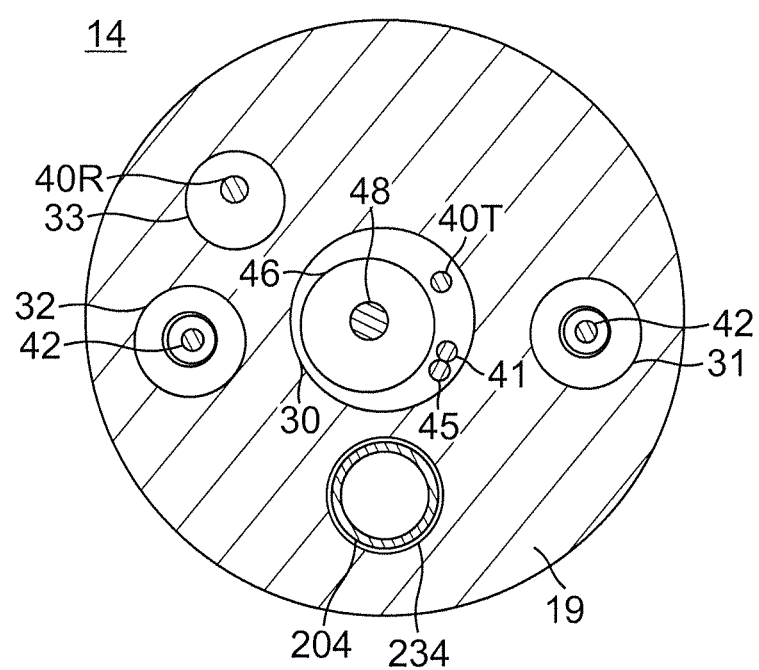
FIG. 5A is an end cross-section view of the distal section of FIG. 5, taken along line A-A.

In an alternate embodiment illustrated in FIGS. 4, 5 and 5A, the catheter has a path 254 for both irrigation and evacuation to allow the catheter to operate between an irrigation mode and an evacuation mode. Structure of the catheter is similar in many respects to the aforementioned embodiment. An irrigation/evacuation (I/E) tubing 204 extends through the control handle 16, the catheter body 12 and the distal section 14 where its distal end is received in a lumen 234 that is in fluid and suction communication with I/E ports 266 in the tip electrode 17 via a fluid passage 262 and transverse branches 264. A proximal end of the tubing 204 is connected to a valve 210, e.g., a 3-way valve with luer fitting 212 and two ports, with port 214 in fluid communication with an infusion pump 216 providing irrigation fluid 218 and port 220 in fluid and suction communication with suction tube 96.

In operation, the valve is positioned so that there is fluid communication between the infusion pump and the I/E tube and no communication between the suction source 90 and the I/E tube so that the catheter can operate in the irrigation mode by providing irrigation at the tissue ablation site. Irrigation fluid enters the catheter and passes into the I/E tubing 204 which extends through the control handle 16, the catheter body 12 and the distal section 14. The fluid then enters the tip electrode 17 via the fluid passage 262, passes through the transverse branches 264 and exits to outside of the tip electrode via the I/E ports 266.

To operate in the evacuation mode, the valve is switched to allow fluid and suction communication between the suction source and the I/E tube and no communication between the infusion pump and the I/E tube. A suction force provided by the suction source 90 draw fluids from the tissue ablation site by means of the suction conduit 94 and deposit the fluids in the collection chamber 92 via the suction tube 96.

To switch between the irrigation mode and the evacuation mode, the operator adjusts the valve accordingly.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. It is further understood that the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An ablation catheter for use with a suction source comprising:
    an elongated catheter body;
    a distal section distal the catheter body, the distal section comprising:
        a tip electrode adapted for ablation and irrigation;
        a multi-lumened member extending between the catheter body and the tip electrode, the multi-lumened member having a first lumen and a second lumen;
        at least one dedicated evacuation port in the tip electrode or in a sidewall of the multi-lumened member, the at least one evacuation port being in suction communication with the first lumen; and
        at least one dedicated irrigation port in the tip electrode in fluid communication with the second lumen; and
    a fluid evacuation path extending at least through the catheter body and the first lumen, the fluid evacuation path configured to provide suction communication between the suction source and the at least one dedicated evacuation port.

2. The catheter of claim 1, wherein the at least one dedicated evacuation port is formed in a sidewall of the multi-lumened member.

3. The catheter of claim 1, wherein the at least one dedicated evacuation port is formed in the tip electrode.

4. The catheter of claim 1, wherein the fluid evacuation path is defined in part by an evacuation tubing extending through the catheter body, the evacuation tubing having a distal end received in the first lumen of the multi-lumened member.

5. The catheter of claim 1, wherein the distal section includes at least one ring electrode proximal of the tip electrode.

6. The catheter of claim 5, wherein the at least one dedicated evacuation port is positioned between the tip electrode and the at least one ring electrode.

7. The catheter of claim 1, further comprising an irrigation fluid path extending through the catheter body and the second lumen of the distal section, the irrigation fluid path configured to pass fluid into the tip electrode.

8. The catheter of claim 1, wherein the at least one dedicated evacuation port comprises a plurality of evacuation ports.

9. The catheter of claim 8, wherein the plurality of evacuation ports range between about two and ten.

* * * * *